US00PP32321P2

(12) United States Plant Patent
Miner et al.

(10) Patent No.: US PP32,321 P2
(45) Date of Patent: Oct. 13, 2020

(54) ***EUPHORBIA* PLANT NAMED 'KM-MM024'**

(50) Latin Name: ***Euphorbia* hybrid**
Varietal Denomination: KM-MM024

(71) Applicants: Keith A. Miner, Lincoln, CA (US); Jennifer Dixson Miner, Lincoln, CA (US)

(72) Inventors: Keith A. Miner, Lincoln, CA (US); Jennifer Dixson Miner, Lincoln, CA (US)

( * ) Notice: Subject to any disclaimer, the term of this patent is extended or adjusted under 35 U.S.C. 154(b) by 0 days.

(21) Appl. No.: 16/602,522

(22) Filed: Oct. 23, 2019

(51) Int. Cl.
*A01H 6/38* (2018.01)
*A01H 5/02* (2018.01)

(52) U.S. Cl.
USPC ..... Plt./302
CPC ..... *A01H 6/385* (2018.05)

(58) Field of Classification Search
USPC ..... Plt./302
CPC ..... A01H 6/385; A01H 6/38; A01H 5/02
See application file for complete search history.

*Primary Examiner* — Keith O. Robinson
(74) *Attorney, Agent, or Firm* — Penny J. Aguirre

(57) ABSTRACT

A new cultivar of *Euphorbia* plant named 'KM-MM024' that is characterized by its new foliage and stems that are dark burgundy red in color with the foliage changing to very deep burgundy color in colder weather, its strong upright stems that do not lodge, its strong and vigorous basal stems, and its flower bracts that are bright yellow in spring.

2 Drawing Sheets

Botanical classification: *Euphorbia* hybrid.
Varietal denomination: 'KM-MM024'.

BACKGROUND OF THE INVENTION

The present invention relates to a new and distinct cultivar of *Euphorbia* of hybrid origin and will be referred to hereafter by its cultivar name, 'KM-MM024'. 'KM-MM024' represents a new herbaceous perennial grown for landscape and container use.

The new cultivar was discovered as a chance seedling by the Inventors in spring of 2015 growing outdoors in a garden in Plumas Lake, Calif. The parents of the new cultivar are unknown, however *Euphorbia amygdaloides* 'Purpurea' (not patented) and *Euphorbia characias* x *martinii* 'Nothowlee' (U.S. Plant Pat. No. 17,178) are thought to be possible parents based on their proximity to the discovered seedling and the characteristics of the new cultivar.

Asexual propagation of the new cultivar was first accomplished by stem cuttings by the Inventor in fall of 2015 in Watsonville, Calif. Asexual propagation by stem cuttings has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'KM-MM024' as a new and unique cultivar of *Euphorbia*.

1. 'KM-MM024' exhibits new foliage and stems that are dark burgundy red in color with the foliage changing to very deep burgundy color in colder weather.
2. 'KM-MM024' exhibits strong upright stems that do not lodge.

3. 'KM-MM024' exhibits strong and vigorous basal stems.
4. 'KM-MM024' exhibits flower bracts that are bright yellow in spring.

'Purpurea', a possible parent plant of 'KM-MM024', is similar to 'KM-MM024' in having new foliage that is burgundy-red in color. 'Purpurea' differs from 'KM-MM024' in having a smaller plant size, weaker stems and in bing more susceptable to plant diseases. 'Northowlee', a possible parent plant of 'KM-MM024', is similar to 'KM-MM024' in having dark burgundy foliage, but differs from 'KM-MM024' in having foliage that is more green when grown in shade and that does not turn darker burgundy in cold weather, in having a smaller plant size and in being more prone to disease and more difficult to propagate. 'KM-MM024' can also be compared to the *Euphorbia amygdaloides* cultivar 'Waleuphglo' (U.S. Plant Pat. No. 22,200). 'Waleuphglo' is similar to 'KM-MM024' in having new foliage that is burgundy-red in color and flower bracts that are yellow in color. 'Waleuphglo' differs from 'KM-MM024' in having a smaller plant size, a less vigorous plant habit, foliage that is lighter burgundy-red in color and foliage that is greener in color in the summer.

BRIEF DESCRIPTION OF THE DRAWINGS

The accompanying colored photographs illustrate the overall appearance and distinct characteristics of the new *Euphorbia*. The photographs were taken of plants as grown in Watsonville, Calif. The photographs in FIG. 1 and FIG. 2 were taken of plants about 1 year in age as grown outdoors.

Figure 1:
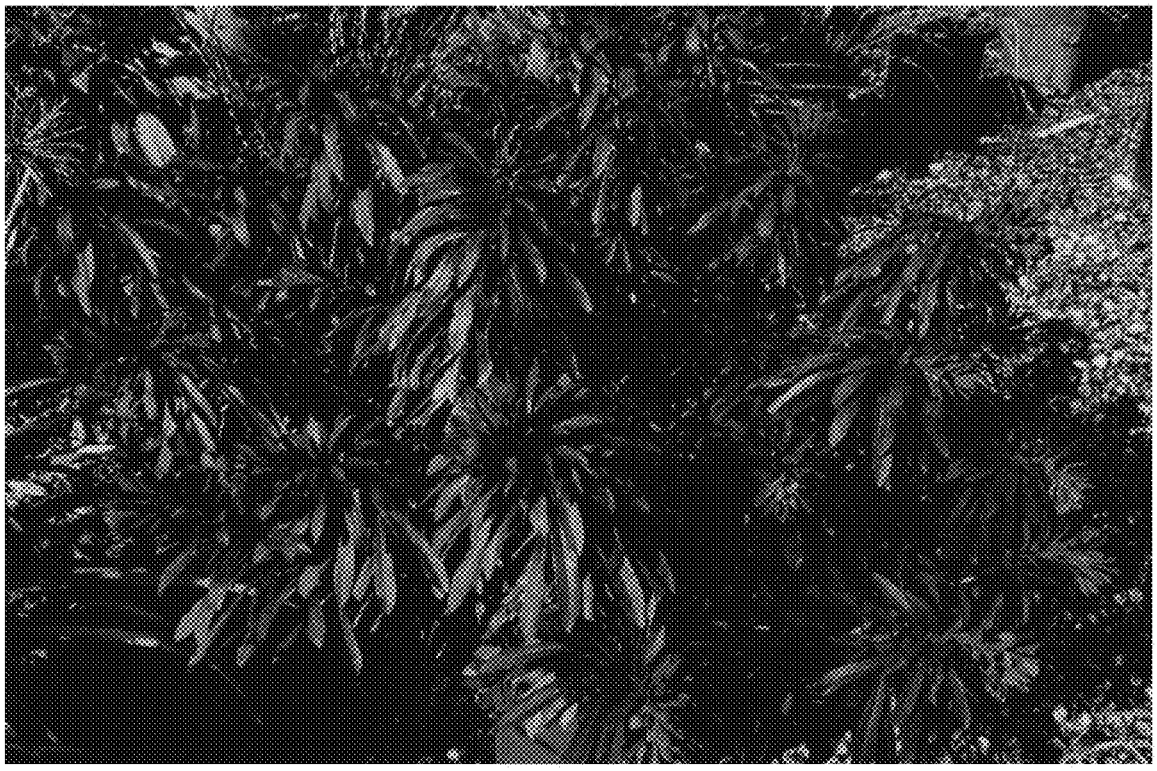
FIG. 1 provides a side view of the plant habit and foliage coloration of the growing tips in spring of 'KM-MM024'.
Figure 2:
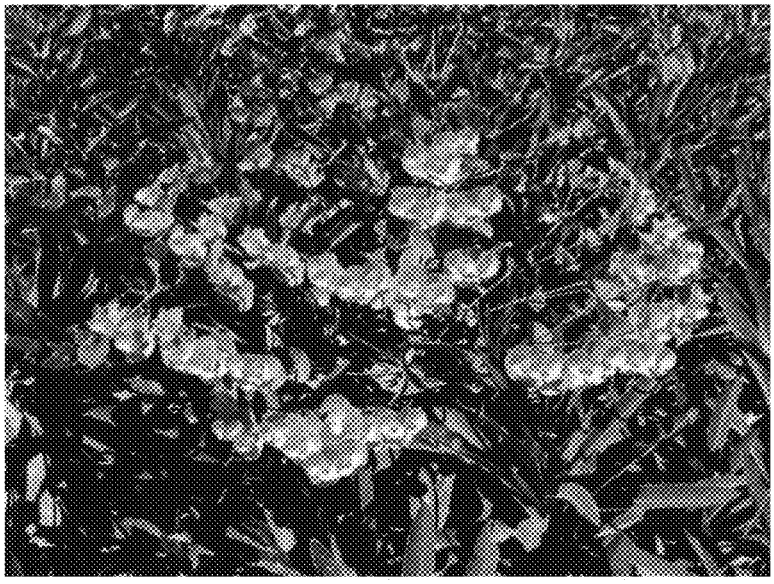

The photograph in FIG. 2 provides a close-up view of the flower bracts of 'KM-MM024' in early summer.

Figure 3:
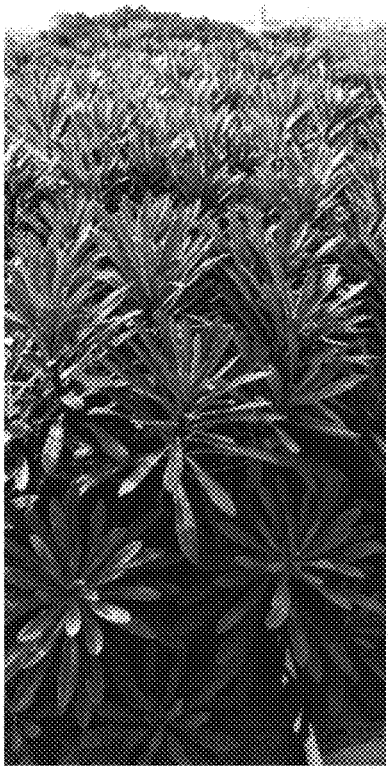

The photograph in FIG. 3 was taken of plants about 6 months in age as grown in one-gallon containers in a greenhouse and provides a view of the foliage of 'KM-MM024' in summer.

The colors in the photographs are as close as possible with the photographic and printing technology utilized and the color values cited in the detailed botanical description accurately describe the colors of the new *Euphorbia*.

DETAILED BOTANICAL DESCRIPTION OF THE PLANT

The following is a detailed description of 9-month-old plants of the new cultivar as grown outdoors in a one-gallon container in Watsonville, Calif. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—May through July in Watsonville, Calif.

*Plant type*.—Herbaceous perennial.

*Plant habit*.—Upright with strong stems.

*Height and spread*.—An average of 54 cm in height and 45 cm in width, as a mature plant in the landscape an average of 61 cm in height and width.

*Cold Hardiness*.—At least to U.S.D.A. Zones 6 to 11.

*Diseases and pests*.—No susceptibility or resistance to specific diseases or pests has been identified but plants has been observed to be disease free.

*Root description*.—Fine, fibrous, 155D in color.

*Root development*.—Average of 10 days to initiate roots and a young rooted plant is produced in about 7 weeks.

*Propagation type*.—Stem cuttings.

*Growth rate*.—Vigorous.

Stem description:

*Stem shape*.—Rounded.

*Stem color*.—Summer: young stems; 183A, mature stems; a blend of 183A and 185A, fall: young stems; 185A, mature stems; 185B to 185C.

*Stem size*.—Main branches; average of 24 cm in length, 7 mm in width, lateral branches; average of 20 cm in length (including inflorescence) and 2 mm in width.

*Stem surface*.—Summer: young and mature stems; densely covered with pubescent hair that matches the surface color and are 0.5 mm in length, mature stems; sparsely covered with bundle scars, an average of 10 scars per stem, linear in shape and 200A in color, old wood; rugose and dull, slightly exfoliating.

*Stem aspect*.—Ranging between being held upright (90°=vertical) and bowing out at the center and growing inward at the top, shorter stems held at an angle of 30° (90°=vertical).

*Stem strength*.—Flexible but strong.

*Internode length*.—An average of 5 mm at mid stem.

*Branching habit*.—Freely branching, 12 main branches, lateral branches develop from crown, an average of 9 per main branch.

Foliage description:

*Leaf shape*.—Linear-oblanceolate.

*Leaf division*.—Simple.

*Leaf base*.—Attenuate.

*Leaf apex*.—Acute.

*Leaf venation*.—Pinnate, mid rib upper surface color; 142A, mid rib lower surface color; changes color as the leaf matures from 142B to 183A.

*Leaf margins*.—Entire and densely covered with minute downy hairs NN155C in color, less than 0.5 mm in length.

*Leaf attachment*.—Sessile.

*Leaf arrangement*.—Whorled.

*Leaf surface*.—Young and mature leaves upper and lower surface; dull, rough to the tough and densely covered with tiny downy hairs that match the leaf color and <0.5 mm in length.

*Leaf color*.—Summer foliage: young leaves upper surface; 144A, margins 182A, young leaves lower surface; 182A and 185B, when held in the sun leaves look closest to a blend of N163A and 163A, mature leaves upper surface; ranging between 147A and 144A, becoming flushed with and changing to, mature leaves lower surface; 144A, becoming flushed with and changing to 183A, fall foliage: young leaves upper surface; a blend of 184A, 187A and 178A, center vein 185A, young leaves lower surface; 183A and 187A, mature leaves upper surface; NN137A, base flushed with 185B, mature leaves lower surface; 147A, base flushed with 185B.

*Leaf number*.—Average of 70 per lateral branch.

*Leaf size*.—Up to 11 cm in length and 1 cm in width.

Flower description:

*Inflorescence type*.—Umbel-like compound terminal cyme with single cymes on lower axils.

*Flower fragrance*.—None.

*Inflorescence*.—Average of 14 days.

*Inflorescence size*.—24 cm in length and 10 cm in width with individual cymes an average of 2 cm in height and width.

*Flower type*.—Cyathium comprised of a cup-shaped involucre surrounding nectary, a female flower and reduced male flowers, asepalous and apetalous.

*Cyathia quantity*.—Average of 17 per lateral stem.

*Cyathia aspect*.—Held straight outward to drooping.

*Cyathia size*.—An average of 1 cm in depth and diameter.

*Peduncles*.—An average of 6 per terminal compound cyme and one per axillary cymes, an average of 3 cm in length and 1 mm in width, held in an average angle of 60° (90°=vertical), moderate strength, 181A and 144A in color, in fall changing to 178A in color, surface is slightly glossy and sparsely covered with pubescent hairs that match surface color and are 0.5 mm in length.

*Pedicels* (*stem of cyathia*).—An average of 2 per peduncle, average of 7 mm in length and 0.5 mm in width, held slightly outward to downward in an average angle of 40° (90°=vertical), low strength, 144B, sometimes flushed with 181A in color, in fall changing to 178A in color, surface is slightly glossy and glabrous.

*Nectaries*.—4 per cyathia, flattened, crescent shaped glands each with 2 narrowly acute tips fused into the base of the flower, 1 mm in length and width, outer surface is 144B, surfaces are glabrous and rubbery.

*Floral bracts*.—2 opposite at base of cymes, mirrored, obicular in shape, rounded and slight cuspidate apex, fused base, inner and outer glabrous and smooth surfaces, entire margins, 144A, sometimes flushed with 182A in color, 6 in whorl at base of terminal compound cyme; an average of 6, spring color; upper and lower surface color when opening and fully open a blend of 1B and 145A, summer color; upper and lower surface color when opening and fully open; 144A, sometimes flushed with 182A, fall color; upper surface 137B, lower surface 180B to 180C, 1.5 cm in length and 1 cm in width, both surfaces are glabrous, obovate in shape, cuneate base, round apex with very small cuspidate tip.

*Involucral bracts.*—2, upper and lower surface color; 144A, sometimes flushed with 182A in color, fall color; upper and lower surface both 137B., lower surface flushed with 180B to 180C, 1 cm in length and width, both surfaces are glabrous.

Reproductive organs:

*Gynoecium.*—One per central female flower (apetalous and asepalous), pistil 3-parted with bifid stigmas an average of 1 mm in length and 0.5 mm in with and 184A in color, style 0.5 mm in width and 162C in color, ovary; urn-shaped shape, 2 mm in length, 1 mm in diameter and 145C in color, pubescent surface.

*Androecium.*—An average of 4 reduced stamens, oval in shape and bi-lobed, 1 mm in length, 145C in color, no pollen was observed.

*Fruit/seed.*—No fruit or seed has been observed.

It is claimed:

1. A new and distinct cultivar of *Euphorbia* plant named 'KM-MM024' as herein illustrated and described.

* * * * *